(12) United States Patent
Sakuda et al.

(10) Patent No.: US 8,383,547 B2
(45) Date of Patent: Feb. 26, 2013

(54) AFLATOXIN PRODUCTION INHIBITOR AND METHOD FOR CONTROLLING AFLATOXIN CONTAMINATION USING THE SAME

(75) Inventors: Shohei Sakuda, Tokyo (JP); Keita Nakamura, Tokyo (JP); Tetsuo Akiyama, Tokyo (JP); Yoshikazu Takahashi, Tokyo (JP); Yasuhiko Muraoka, Tokyo (JP); Ikuko Kurata, Tokyo (JP)

(73) Assignees: Microbial Chemistry Research Foundation, Tokyo (JP); The University of Tokyo, Tokyo (JP)

( * ) Notice: Subject to any disclaimer, the term of this patent is extended or adjusted under 35 U.S.C. 154(b) by 0 days.

(21) Appl. No.: 13/329,473

(22) Filed: Dec. 19, 2011

(65) Prior Publication Data

US 2012/0190746 A1    Jul. 26, 2012

Related U.S. Application Data

(62) Division of application No. 11/922,703, filed as application No. PCT/JP2006/311881 on Jun. 13, 2006, now abandoned.

(30) Foreign Application Priority Data

Jun. 23, 2005  (JP) .................. 2005-183964
Jan. 24, 2006  (JP) .................. 2006-015537

(51) Int. Cl.
*A01N 25/00*      (2006.01)
*A01N 63/00*      (2006.01)
*C07C 229/00*     (2006.01)
(52) U.S. Cl. .............. 504/117; 424/405; 562/561
(58) Field of Classification Search .............. None
See application file for complete search history.

(56) References Cited

FOREIGN PATENT DOCUMENTS

| JP | 03-077857 | 4/1991 |
| JP | 09-241167 | 9/1997 |
| JP | 11-079911 | 3/1999 |
| JP | 2001-139507 | 5/2001 |

OTHER PUBLICATIONS

STN Accession No. 1992-19735. Abstract of Takeuchi et al. (JP 03077857). Retrieved from STN Aug. 24, 2011. 2 pages.
International Search Report issued on Sep. 5, 2006 in PCT/JP2006/311881.

*Primary Examiner* — Leslie A. Royds Draper
(74) *Attorney, Agent, or Firm* — Edwards Wildman Palmer LLP; James E. Armstrong, IV (57) ABSTRACT

The present invention relates to provide an aflatoxin production inhibitor that inhibits aflatoxin production specifically and efficiently, is highly safe, and is practical, and an efficient production method thereof; and a method for controlling aflatoxin contamination that uses the aflatoxin production inhibitor, specifically relating to an aflatoxin production inhibitor that includes at least one of a dioctatin represented by the following formula (I) and a derivative thereof, as an active ingredient:

formula (I)

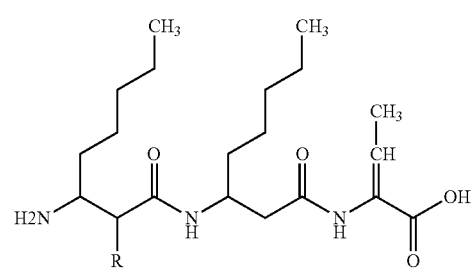

where, in the formula (I), R represents one of hydrogen and a methyl group.

5 Claims, 4 Drawing Sheets

AFLATOXIN PRODUCTION INHIBITOR AND METHOD FOR CONTROLLING AFLATOXIN CONTAMINATION USING THE SAME

CROSS REFERENCE TO RELATED APPLICATIONS:

This application is a Divisional Application of U.S. patent application Ser. No. 11/922,703, filed Feb. 17, 2009, which is a 371 US National Phase Application of PCT/JP2006/311881, filed Jun. 13, 2006, which claims priority to Japanese Patent Application No. JP 2005-183964, filed Jun. 23, 2005, and Japanese Patent Application No. JP 2006-015537, filed Jan. 24, 2006, the disclosures of each of which are expressly incorporated herein by reference in their entireties.

TECHNICAL FIELD

The present invention relates to an aflatoxin production inhibitor that comprises at least one of dioctatin and derivatives thereof as an active ingredient, and a production method thereof; and a method for controlling aflatoxin contamination that uses the aflatoxin production inhibitor.

BACKGROUND ART

While secondary metabolites of the fungus include useful compounds, they also include many compounds that present toxicity, called mycotoxin. At present, mycotoxin contamination of crops has become a serious problem all over the world. In order to obtain a safe food and ensure a stable supply thereof, there is a need for ways to control mycotoxin contamination.

Among mycotoxin contamination of crops, the most serious one is aflatoxin contamination of crops. It is known that aflatoxin is the strongest carcinogenic substance of the known natural substances. Since aflatoxin is a compound that is not degraded by a normal food preparation method, etc., the value of the compound allowed to be contaminated in crops is regulated to as low as 10 ppb. Thus, the loss due to the disposal of crops contaminated with aflatoxin reaches a large amount.

Aflatoxin is mainly produced by strains of *Aspergillus flavus*, and *A. parasiticus*, and is known to infect crops such as maize and peanut and produce aflatoxin under the tropical and subtropical environments (See, Non-Patent Literatures 1 and 2). Due to the climate change by the global warming in recent years, it is concerned that contamination may extend to the region with a climate other than tropical and subtropical climates.

In order to control aflatoxin contamination, basic research such as genomic analysis of aflatoxin-producing microorganism and identification of a gene that is involved in the production, and practical research such as acquisition of variety with resistance to infection and reduction of contamination by the competition with aflatoxin non-producing microorganism have been conducted. However, an efficient and drastic method for controlling aflatoxin contamination has not yet been established.

Possible methods for controlling aflatoxin contamination include, for example, a method in which an antifungal agent that inhibits the growth of aflatoxin-producing microorganism. However, strong antifungal agents have a problem in terms of safety. In addition, there is a possibility that the spread of strain resistant to the antifungal agents is caused.

Since aflatoxin is a secondary metabolite, it is considered that inhibition of the production thereof does not affect the growth of aflatoxin-producing microorganism. Thus, if a medical agent that inhibits only the production of aflatoxin specifically is available, such medical agent could provide an effective method for controlling contamination.

As a result of search for the substances that inhibit the production of aflatoxin, it was found that dichlorvos, an organophosphorus insecticide, and tricyclazole which inhibits melanin biosynthetic enzyme, have aflatoxin production inhibitory activity (See, Non-Patent Literature 3). However, these compounds have not come into practical use because the aflatoxin production inhibitory activity of these compounds is weak and there is a concern over the safety of the compounds themselves. In addition, there is a problem in selectivity of the inhibitory activity.

As mentioned above, there is a need for compounds that do not cause the spread of resistant strain and have an action to inhibit only aflatoxin production specifically. As a result of search, some compounds are found (Patent Literatures 1 and 2); however, in the present situation, an acceptable aflatoxin production inhibitor that is highly safe and is of practical use has not been found yet.

Patent Literature 1: Japanese Patent Application Laid-Open (JP-A) No. 09-241167
Patent Literature 2: JP-A No. 11-79911
Non-Patent Literature 1: Council for Agricultural Science and Technology., "Mycotoxins: Risks in Plant, Animal, and Human Systems", CAST, Ames, Iowa, USA, 2003
Non-Patent Literature 2: Shun-ichi Udagawa, Setsuko Tabata, and Mitsuo Nakazato, "Mycotoxin", Chuohoki, 2002
Non-Patent Literature 3: L. L. Zaika and R. L. Buchanan, J. Food. Prot., 50, 691 (1987)

DISCLOSURE OF INVENTION

An object of the present invention is to solve the conventional problems and to achieve the following objects. Specifically, an object of the present invention is to provide an aflatoxin production inhibitor that inhibits aflatoxin production specifically and efficiently, is highly safe, and is practical, and an efficient production method thereof; and a method for controlling aflatoxin contamination that uses the aflatoxin production inhibitor.

As a result of dedicated investigations conducted by the present inventors to settle the above-mentioned problems, they have made the following findings. Specifically, as a result of search for substances that inhibit aflatoxin production specifically, they have found that dioctatin, which is a known biologically active substance, inhibits aflatoxin production without inhibiting the growth of aflatoxin-producing microorganism.

Dioctatin is a compound that was isolated from the culture of *Streptomyces* sp. SA-2581 and has a low toxicity. As the bioactivity thereof, dioctatin is known to have immunosuppression activity through inhibition of dipeptidyl aminopeptidase II (DPP II).

However, it has not been known at all that dioctatin is capable of inhibiting aflatoxin production, which is a new finding by the present inventors.

In addition, dioctatin has an asymmetric carbon and an isomer can exist. The configuration of a natural form of dioctatin, isolated from the culture of dioctatin-producing microorganism, is not known, and the configuration of the natural form of dioctatin and a method for producing dioctatin having the configuration are also new findings by the present inventors.

The present invention is based on the above-mentioned findings by the present inventors, and means for solving the above-mentioned problems are as follows. Specifically,

<1> An aflatoxin production inhibitor including at least one of a dioctatin represented by the following formula (I) and a derivative thereof, as an active ingredient:

formula (I)

wherein, in the formula (I), R represents one of hydrogen and a methyl group.

<2> The aflatoxin production inhibitor according to the <1>, wherein the dioctatin is dioctatin A represented by the following formula (Ia):

formula (Ia)

<3> The aflatoxin production inhibitor according to the <1>, wherein the dioctatin is dioctatin A represented by the following formula (II):

formula (II)

<4> The aflatoxin production inhibitor according to the <1>, wherein the dioctatin is dioctatin B represented by the following formula (III):

formula (III)

<5> A method for producing an aflatoxin production inhibitor, including: culturing a dioctatin-producing microorganism belonging to the genus *Streptomyces*; and at least one of separating and purifying dioctatin from a culture obtained, by centrifugal liquid liquid partition chromatography.

<6> The method for producing an aflatoxin production inhibitor according to the <5>, wherein the dioctatin-producing microorganism is an actinomycete, *Streptomyces* sp. SA-2581.

<7> A method for producing an aflatoxin production inhibitor, including synthesizing the dioctatin of one of the <3> and <4> by chemical synthesis.

<8> The method for producing an aflatoxin production inhibitor according to the <7>, wherein the dioctatin of the <3> is synthesized using threonine, S-form of 3-aminooctanoic acid, and S-form of 3-amino-2-methyloctanoic acid.

<9> The method for producing an aflatoxin production inhibitor according to the <7>, wherein the dioctatin of the <4> is synthesized using threonine and S-form of 3-aminooctanoic acid.

<10> A method for controlling aflatoxin contamination, including using the aflatoxin production inhibitor of any one of the <1> to <4> to thereby inhibit aflatoxin production by an aflatoxin-producing microorganism.

<11> The method for controlling aflatoxin contamination according to the <10>, wherein the aflatoxin production inhibitor is administered to a crop to thereby inhibit aflatoxin production by the aflatoxin-producing microorganism which has infected the crop.

<12> The method for controlling aflatoxin contamination according to the <11>, wherein the crop is at least one selected from grains, nuts, spices, and pulse.

<13> The method for controlling aflatoxin contamination according to the <10>, wherein the aflatoxin production inhibitor is applied to a plant to thereby suppress aflatoxin production by the aflatoxin-producing microorganism which has infected the plant.

The present invention can solve the conventional problems and provide an aflatoxin production inhibitor that inhibits aflatoxin production specifically and efficiently, is highly safe, and is practical, and an efficient production method thereof; and a method for controlling aflatoxin contamination that uses the aflatoxin production inhibitor.

BEST

Figure 1:
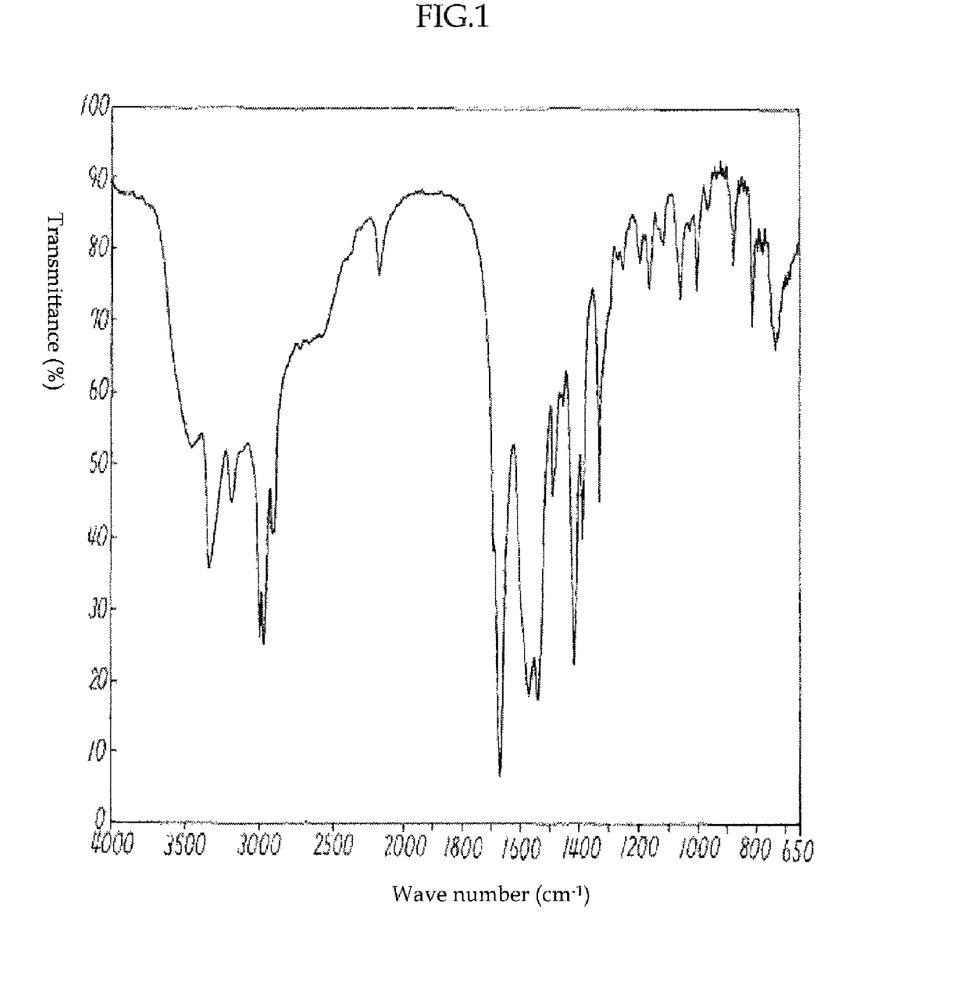
FIG. 1 is a chart of an infrared absorption spectrum of dioctatin A in a potassium bromide pellet, and the horizontal axis shows wave number ($cm^{-1}$) and the vertical axis transmittance (%).
Figure 2:
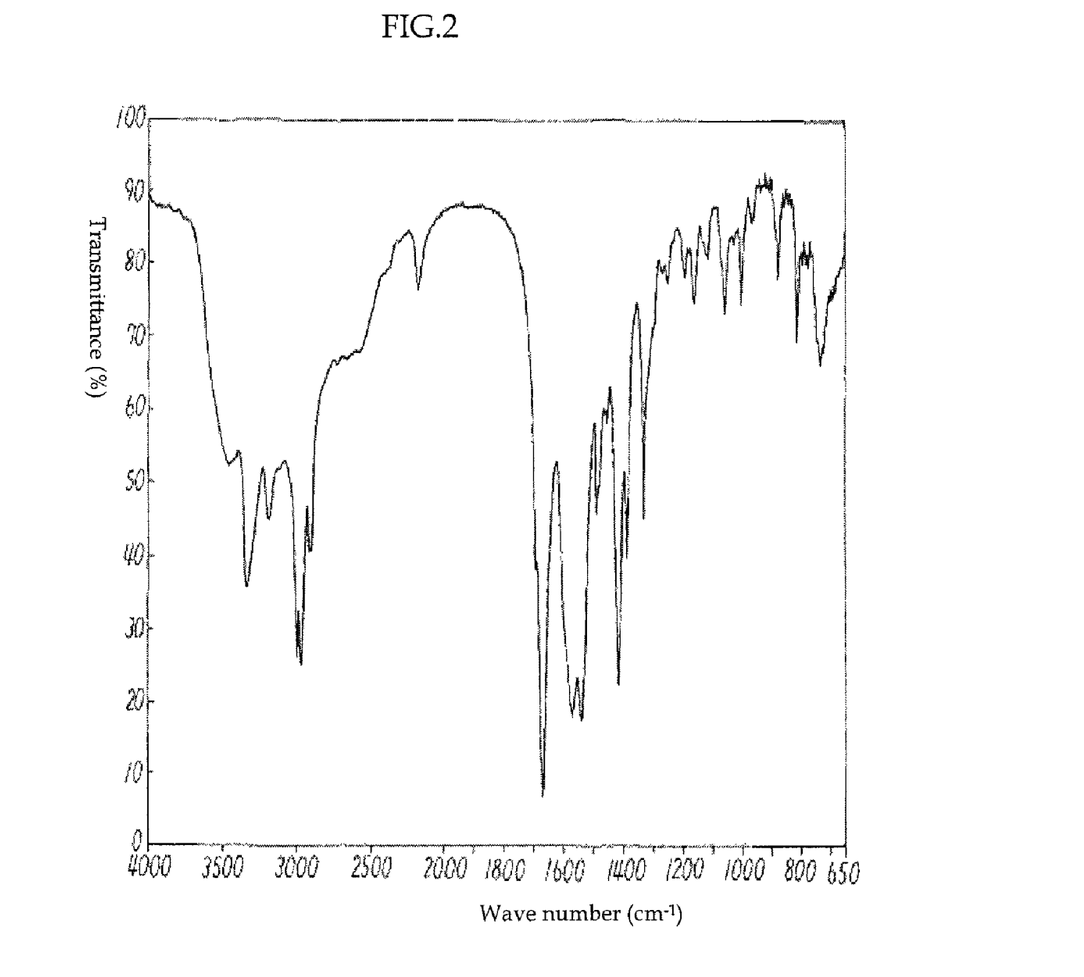
FIG. 2 is a chart of an infrared absorption spectrum of dioctatin B in a potassium bromide pellet, and the horizontal axis shows wave number ($cm^{-1}$) and the vertical axis transmittance (%).
Figure 3:
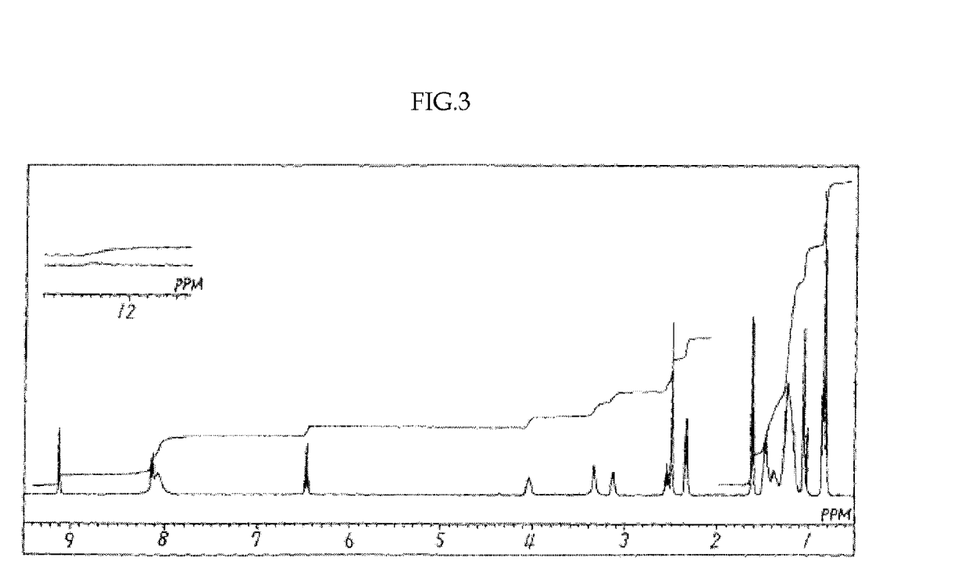
FIG. 3 is a chart of a proton nuclear magnetic resonance spectrum of dioctatin A hydrochloride in deuterated dimethyl sulfoxide at 400 MHz, and the horizontal axis shows chemical shift (ppm). The internal standard is tetramethylsilane.
Figure 4:
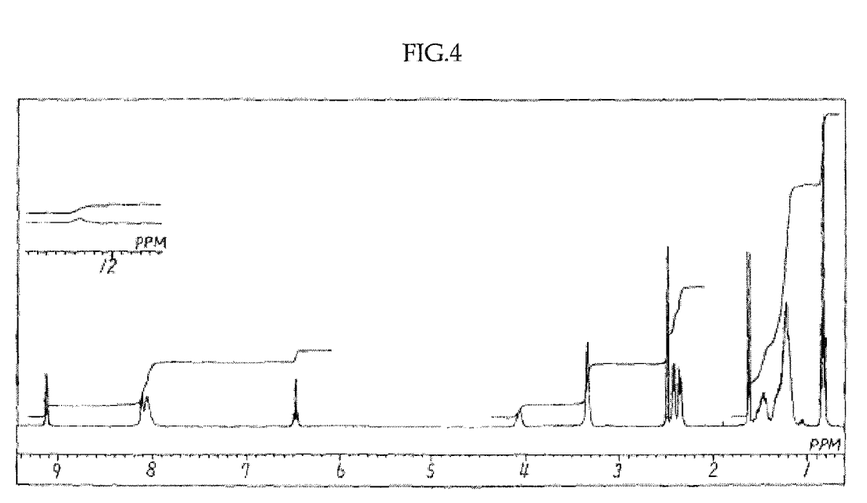
FIG. 4 is a chart of a proton nuclear magnetic resonance spectrum of dioctatin B hydrochloride in deuterated dimethyl sulfoxide at 400 MHz, and the horizontal axis shows chemical shift (ppm). The internal standard is tetramethylsilane.

—Dioctatin B—
(1) The appearance is white powder.
(2) The melting point is from 251° C. to 252° C.
(3) The mass, determined by secondary ion mass spectrometry (SIMS), is 384(M+1)$^+$.
(4) The molecular formula is $C_{20}H_{37}N_3O_4$, and the molecular mass is 383.5.
(5) The specific rotation is +15.0° (c1, AcOH).
(6) The maximum absorption wavelength in the ultraviolet region, determined in acetonitrile containing 10% (V/V) 0.1 N hydrochloric acid, is 224 nm (log $\epsilon$=3.79).
(7) The maximum absorption wavelength in the infrared region (cm$^{-1}$, KBr pellet) is 3300, 3150, 2970, 2950, 2870, 2150, 1660, 1560, 1540, 1405, 1380, 1320, 1180, 1155, 1120, 1020, 980, 870, 795, 730. FIG. 2 shows the spectrum.
(8) The proton nuclear magnetic resonance spectrum of dioctatin B hydrochloride in deuterated dimethyl sulfoxide at 400 MHz is as shown in FIG. 4.
(9) The $^{13}C$ nuclear magnetic resonance spectrum of dioctatin B hydrochloride in deuterated dimethyl sulfoxide at 100 MHz is as shown in Table 1 below.
(10) Soluble in acidic methanol, acidic ethanol, acidic acetonitrile, acidic dimethyl sulfoxide, and acetic acid; poorly-soluble in water, methanol, ethanol, acetonitrile, and dimethyl sulfoxide; and insoluble in ethyl acetate, benzene, chloroform, and ethyl ether.
(11) A neutral amphoteric substance.
(12) When subjected to thin layer chromatography using a silica gel 60 plate (Art. 5715, manufactured by Merck & Co., Inc.), and chloroform:methanol:acetic acid=10:3:1 (by volume) as a developing solvent, the Rf value is 0.64.

TABLE 1

| Dioctatin A | | Dioctatin B | |
|---|---|---|---|
| 172.9 ppm | s | 168.9 ppm | s |
| 168.8 | s | 168.5 | s |
| 165.5 | s | 165.5 | s |
| 131.3 | d | 131.4 | d |
| 128.6 | s | 128.6 | s |
| 52.5 | d | 48.2 | d |
| 46.1 | t | 46.2 | d |
| 40.9 | d | 40.6 | t |
| 40.5 | t | 37.5 | t |
| 33.6 | t | 33.6 | t |
| 31.1 | t | 31.9 | t |
| 31.1 | t | 31.1 | t |
| 30.8 | t | 31.0 | t |
| 25.0 | t | 25.0 | t |
| 23.7 | t | 24.0 | t |
| 22.0 | t | 22.0 | t |
| 21.8 | t | 21.8 | t |
| 14.0 | q | 13.9 | q |
| 13.9 | q | 13.8 | q |
| 13.8 | q | 13.5 | q |
| 13.5 | q | | |

In Table 1, "s", "d", "t", and "q" represent a singlet, a doublet, a triplet, and a quartet, respectively. The internal reference is tetramethylsilane.

The derivative is not particularly limited and can be appropriately selected according to the purpose. Examples thereof include salts of the dioctatin formed with a pharmaceutically acceptable cation at the carboxyl group of the dioctatin, salts of the dioctatin formed with a pharmaceutically acceptable anion at the amino group of the dioctatin, and the like.

Examples of the cation include alkaline metals such as sodium and potassium, alkaline earth metals such as calcium and magnesium, and the like. Examples of the anion include hydrochloric acid, sulfuric acid, phosphoric acid, and the like.

The salts may be used alone or in combination.

The dioctatin, an active ingredient of the aflatoxin production inhibitor, is a low toxic substance. In the acute toxicity test in mice, no death was observed when 250 mg/kg of dioctatin A, or 250 mg/kg of dioctatin B was administered to mice intraperitoneally.

The aflatoxin production inhibitor is not particularly limited as long as it comprises at least one of the dioctatin and the derivatives thereof (hereinafter referred to as "dioctatin compound", and the aflatoxin production inhibitor may comprise other components appropriately selected according to the purpose, such as a carrier.

The form of the aflatoxin production inhibitor is not particularly limited and can be appropriately selected according to the purpose. For example, the aflatoxin production inhibitor can be formulated using a known carrier used for pharmaceutical agents and preparations for farming and gardening. Examples of the form include solid formulations, powders, tablets, capsules, granules, liquid formulations, gels, creams, and spray agents.

(Method for Producing Aflatoxin Production Inhibitor)

The method for producing an aflatoxin production inhibitor comprises a step in which dioctatin is prepared, and other steps appropriately selected according to necessity.

The step in which dioctatin is prepared include a first aspect in which dioctatin is separated and/or purified from the culture of dioctatin-producing microorganism, and a second aspect in which dioctatin is chemically synthesized.

Dioctatin compounds, prepared by one of the first aspect and the second aspect, may be used as the aflatoxin production inhibitor of the present invention without further treatment. Alternatively, by adding appropriately other components to the dioctatin compounds in the other step, the aflatoxin production inhibitor of the present invention may be prepared.

<Preparation of Dioctatin>

<<First Aspect>>

In the first aspect of the step in which dioctatin is prepared, the dioctatin-producing microorganism belonging to the genus *Streptomyces* is cultured, and dioctatin is separated and/or purified from the culture obtained.

—Dioctatin-Producing Microorganism—

The dioctatin-producing microorganism is not particularly limited as long as it is capable of producing the dioctatin, and can be appropriately selected according to the purpose. The genus *Streptomyces* is preferable that is an actinomycete with a hyphal width of around 1 μm and has mycological properties as follows. Under the light microscope, the spore chain on the aerial hypha of actinomycete is open spiral. Under the electron microscope, rod-shaped spore is observed. The spore surface is smooth. As a cell wall component, L,L-diaminopimelic acid is detected. Even under the electron microscope, sporangia and other characteristic structures are not observed. Of the genus *Streptomyces, Streptomyces* sp. is more preferable, and SA-2581 strain (*Streptomyces* sp. SA-2581) is most preferable.

The growth characteristics and the cultural properties of the SA-2581 strain on various media are as shown in Table 2 below. For the description of color below, the standard given in parenthesis is in accordance with the Color Harmony Manual of Container Corporation of America. Evaluations were performed after cultivation at 27° C. for two weeks.

TABLE 2

| Medium | Growth | Color of aerial hypha | Color of reverse of colony | Production of soluble pigment |
|---|---|---|---|---|
| Sucrose-nitrate agar | Poor | White (a) | White to pale yellow | None |
| Glucose-asparagine agar | Satisfactory | White (a) | Pale yellowish brown | None |
| Yeast-malt agar | Abundant | White to gray (a to 3ba) | Pale yellowish brown | Pale brown |
| Oat meal agar | Satisfactory | Gray (3ba) | Pale orange | Pale brown |
| Starch-inorganic salt agar | Abundant | Gray (3ba) | Pale orange | None |
| Glycerin-asparagine agar | Abundant | Gray (3ba) | Pale orange | Pale brown |
| Peptone-yeast extract-iron agar | Abundant | Gray (3ba) | Yellowish brown | Pale brown |
| Tyrosine agar | Satisfactory | Gray (3ba) | Yellowish brown | Pale brown |
| Nutrient agar | Abundant | Gray (5ba) | Pale orange to dull orange | Pale brown |

The physiological properties of the SA-2581 strain are as shown in Table 3 below. Whether the SA-2581 strain has an ability to utilize sugar or not is as shown in Table 4 below. Evaluations were performed after cultivation at 27° C. for two weeks.

TABLE 3

| Physiological properties | |
|---|---|
| Gelatin liquefaction | Positive |
| Starch hydrolysis | Positive |
| Casein hydrolysis | Positive |
| Urea hydrolysis | Positive |
| Esculin hydrolysis | Negative |
| Catalase test | Positive |
| Cellulase activity | Negative |
| Tyrosinase activity | Positive |
| Reduction of nitrate | Positive |
| Peptonization of skim milk | Positive |
| Coagulation of skim milk | Negative |
| Production of hydrogen sulfide | Negative |
| Salt resistance concentration | 6% |
| Growth temperature | 15° C. to 34° C. |

TABLE 4

| Sugar | Utilization |
|---|---|
| D-glucose | Positive |
| D-fructose | Positive |
| L-arabinose | Negative |
| D-xylose | Negative |
| L-rhamnose | Positive |
| Sucrose | Doubtfully positive |
| Raffinose | Positive |
| D-mannitol | Positive |
| Inositol | Doubtfully negative |

—Preparation of Culture—

The culture is obtained through cultivation of the dioctatin-producing microorganism by any method without limitation as long as the method involves inoculating the dioctatin-producing microorganism to a medium containing at least nutrient source and allowing it to grow aerobically, and the method can be appropriately selected according to the purpose.

The dioctatin-producing microorganism may be obtained by isolating from nature according to usual method.

The nutrient source is not particularly limited as long as it can be used as a nutrient source of actinomycete, and can be appropriately selected according to the purpose. Examples thereof include nitrogen sources such as peptone, meat extract, corn steep liquor, cottonseed flour, peanut flour, soybean flour, yeast extract, NZ-amine, casein hydrolysate, sodium nitrate, ammonium nitrate and ammonium sulfate; carbohydrates such as glycerin, sucrose, starch, glucose, galactose, mannose and molasses; carbon sources such as fatty acids; inorganic salts such as sodium chloride, phosphate, calcium carbonate and magnesium sulfate, and the like.

In addition to the nutrient source, for example, trace metal salts, and animal, vegetable and mineral oils as an antifoaming agent can also be added as a component in the medium.

Any of these can be advantageously employed if it is utilized by the dioctatin-producing microorganism and is useful for the production of the dioctatin, and all known materials for culturing actinomycete can be used.

The culture method may be any one of solid (agar) culture such as slant culture and plate culture, and liquid culture. In order to allow the production of the dioctatin in large quantity, liquid culture is preferable. The liquid culture may be any one of shaking culture, stationary culture, and stirred culture; shaking culture is preferable and rotary shaking culture is more preferable. In the case of large-scale culture, culture may be carried out using a fermenter or the like.

The cultivation temperature is not particularly limited as long as it is a range in which the dioctatin-producing microorganism grows and produces the dioctatin, can be appropriately selected according to the purpose, and is preferably from 15° C. to 34° C., more preferably from 25° C. to 30° C.

The cultivation period is not particularly limited and can be appropriately selected according to the purpose. Normally, after about 7 days to about 9 days cultivation, the dioctatin-producing microorganism grows sufficiently and produces a sufficient amount of the dioctatin. Whether the dioctatin has been produced in a sufficient amount can be determined, for example, by analyzing with the high-performance liquid chromatography a solution which is prepared by evaporating the butanol extract of the supernatant of culture broth to dryness and concentrating to 1/6 original volume with methanol.

—Separation and/or Purification of Dioctatin—

The method for separating and/or purifying the dioctatin includes methods in which the dioctatin is separated from the culture (fungus body and culture broth), by, for example, solvent extraction process using a solvent, adsorption-separation process that utilizes the differences of adsorption affinity to various adsorbents, gel filtration, chromatography utilizing countercurrent distribution, and centrifugal liquid liquid partition chromatography. These methods may be performed alone or in combination. Separation and/or purification is/are preferably performed using at least centrifugal liquid liquid partition chromatography.

—Centrifugal Liquid Liquid Partition Chromatography—

The separation and/or purification of the dioctatin by the centrifugal liquid liquid partition chromatography are/is preferably performed, for example, as follows. A sample that contains oily residue, obtained by concentration and dryness of the extract prepared from culture broth, is injected into a partition cell in a centrifugal field, into which cell the upper layer and lower layer of chloroform:methanol:water=5:6:4 (by volume) are filled, allowing separation due to the difference in solubility.

Examples of the method for preparing extract from the culture broth include a method that involves extracting with a water-immiscible organic solvent such as butanol at pH 2 or less; a method that involves adsorbing to an organic adsorbent such as Diaion HP-20 and then eluting with acidic hydrous methanol, acidic hydrous acetone, etc.; and the like.

Examples of the method for preparing extract from the fungus body include a method that involves subjecting the fungus body to extraction with an organic solvent such as acidic hydrous methanol, acidic hydrous acetone, etc.; and the like.

Below is shown an example of the process of separation and/or purification using centrifugal liquid liquid partition chromatography.

A stationary phase (the lower layer from chloroform: methanol:0.017 M aqueous ammonia=5:6:4 (by volume)) is filled into a partition cell, the partition cell is rotated, and a mobile phase (the upper layer from chloroform:methanol: 0.017 M aqueous ammonia=5:6:4 (by volume)) is introduced. After the mobile phase has passed out of the exit of the partition cell and the internal pressure of the cell has reached constant, a sample, obtained by concentration and dryness of the extract prepared from culture broth and by dissolving with the mobile phase, is introduced. The mobile phase is kept running, separating a primary purified product that contains the dioctatin due to the difference in solubility and collecting it. Then, 1 M hydrochloric acid is added to the primary purified product until pH 3, and a sample containing dioctatin hydrochloride is prepared.

Subsequently, a stationary phase (the upper layer from chloroform:methanol:water=5:6:4 (by volume)) is filled into the partition cell, the partition cell is rotated, and a mobile phase (the lower layer from chloroform:methanol:water=5: 6:4 (by volume)) is introduced. After the mobile phase has passed out of the exit of the partition cell and the internal pressure of the cell has reached constant, the primary purified product that contains dioctatin hydrochloride is introduced. The mobile phase is kept running, separating a secondary purified product due to the difference in solubility and collecting it. The secondary purified product obtained is washed with water and then with acetone, thereby allowing us to obtain dioctatin hydrochloride as a pure product.

Examples of the method for purifying further the secondary purified product obtained include distillation, liquid extraction, vacuum concentration, reprecipitation, crystallization, and the like. These may be performed alone or two or more of methods may be performed in combination.

<<Second Aspect>>

In the second aspect of the step in which dioctatin is prepared, dioctatin that has a naturally occurring configuration is chemically synthesized. The method for synthesizing the dioctatin is not particularly limited as long as the method can synthesize dioctatins having the configuration represented by the formula (II) or the formula (III), and can be appropriately selected according to the purpose.

Whether the compound obtained is dioctatin that has a naturally occurring configuration can be confirmed by determining if at least one of optical rotation and NMR spectrum corresponds to that of the dioctatin which is obtained in the first aspect. Evaluation of DPPII inhibitory activity also allows confirmation.

—Synthesis of Dioctatin—

Dehydrobutyrine (2-amino-2-butenic acid) that is contained in the dioctatin A and in the dioctatin B is stable only in peptide, and the peptide that contains the dehydrobutyrine can be synthesized through a dehydration reaction of threonine-containing peptide.

The dioctatin A and the dioctatin B can be synthesized by synthesizing peptide from 3-aminooctanoic acid, 3-amino-21-methyloctanoic acid, and threonine, and from 3-aminooctanoic acid and threonine, respectively, then performing a dehydration reaction of threonine properly, and lastly removing a protecting group.

The threonine may be any of D-form, L-form, and DL-form, and may be derivatives such as methyl ester hydrochloride. The threonine may be commercially available one. For the commercially available threonine, L-threonine is preferable in terms of the cost required to obtain it.

An example of synthesis method will be described below.
(1) Preparation of Dioctatin B The dioctatin B that has a naturally occurring configuration can be synthesized using threonine and S-form of 3-aminooctanoic acid as a raw material.

(S)-3-aminooctanoic acid can be obtained as follows. The anion of S—N-benzyl-1-phenylethylamine is added to 2-octenoic acid ester by Michael addition, the resulting adduct anion is quenched by ammonium chloride to obtain a precursor of S-form of 3-aminooctanoic acid. This precursor is subjected to hydrogenolysis to obtain (S)-3-aminooctanoic acid ethyl ester, which is further subjected to hydrolysis to obtain (S)-3-aminooctanoic acid.

Further, the reaction with Boc2O gives S-form of Boc-3-aminooctanoic acid.

First, L-threonine methyl ester hydrochloride and S-form of Boc-3-aminooctanoic acid, prepared as described above, are condensed to obtain dipeptide (Boc-3-aminooctanoyl-L-threonine methyl ester).

The dipeptide obtained is subjected to a dehydration reaction to prepare Boc-3-aminooctanoyl-2-amino-2-butenic acid methyl ester.

For the dehydration reaction, any of acid chlorides and bases may be used. For example, a combination of methanesulfonyl chloride and triethylamine is preferable.

The solvent used for reaction is not particularly limited as long as it is nonaqueous solvent and can dissolve raw materials, and can be appropriately selected according to the purpose. For example, methylene chloride and chloroform that does not contain ethanol are preferable.

Next, the Boc group of the Boc-3-aminooctanoyl-2-amino-2-butenic acid methyl ester is removed, S-form of Boc-3-aminooctanoic acid is condensed again to obtain a protected tripeptide. The method for removing the Boc group is not particularly limited and can be appropriately selected from known methods. Examples of the reagent to be used include trifluoroacetic acid, 4 M hydrochloric acid in dioxane, and the like.

Lastly, the N-terminal Boc group and the C-terminal methyl ester are sequentially removed to thereby obtain dioctatin B that has a naturally occurring configuration.

The dioctatin B with a defined configuration, which is obtained through synthesis using threonine and S-form of 3-aminooctanoic acid as raw materials according to the above-mentioned method, is considered to have the same configuration as that of natural dioctatin B, obtained from the culture of the dioctatin-producing microorganism, since nmr spectrum and optical rotation correspond to those of natural dioctatin B, and has excellent aflatoxin production inhibitory activity as does the natural dioctatin B.

(2) Preparation of Dioctatin A

The dioctatin A that has a naturally occurring configuration can be synthesized using threonine, S-form of 3-aminooctanoic acid, and S-form of 3-amino-2-methyloctanoic acid as a raw material.

S-form of 3-amino-2-methyloctanoic acid can be obtained as follows. The anion of S—N-benzyl-1-phenylethylamine is added to 2-octenoic acid ester by Michael addition, the resulting adduct anion is quenched by methyl iodide to obtain two different stereoisomers of precursor. This mixture is subjected to hydrogenolysis to obtain 3-amino-2-methyloctanoic acid ethyl ester, which is further subjected to hydrolysis to obtain a mixture of (2S,3S) form and (2R,3S) form of 3-amino-2-methyloctanoic acid. The mixture obtained can be separated by chromatography using ion exchange resin. For example, isomers are eluted from a Dowex 50 column with pyridine-acetate buffer, and the isomer eluted earlier and one eluted later have different chemical shifts of methyl group signal in 1H-NMR. Thus, separation of both isomers can be confirmed.

These are each protected with Boc to obtain two different S-forms of Boc-3-amino-2-methyloctanoic acid.

In the same way as in (1) preparation of the dioctatin B, dehydrated dipeptide and Boc-3-aminooctanoyl-2-amino-2-butenic acid methyl ester are synthesized. The second condensation reaction is performed using S-form of Boc-3-amino-2-methyloctanoic acid instead of Boc-3-aminooctanoic acid to obtain a protected tripeptide. Lastly, protecting groups at both ends are removed to thereby obtain dioctatin A.

Among these, dioctatin A, synthesized using S-form of 3-aminooctanoic acid and one of S-forms of 3-amino-2-methyloctanoic acid which is eluted later when subjected to ion exchange resin chromatography, has optical rotation and NMR spectrum that correspond to those of natural dioctatin A obtained from the culture of the dioctatin-producing microorganism. This indicates that the configuration at the 3-position of the 3-amino-2-methyloctanoic acid in the natural dioctatin A is S.

The dioctatin A that has a naturally occurring configuration, which is obtained through synthesis using threonine, S-form of 3-aminooctanoic acid and S-form of 3-amino-2-methyloctanoic acid as raw materials according to the above-mentioned method, has excellent aflatoxin production inhibitory activity as does natural dioctatin A which is obtained from the culture of the dioctatin-producing microorganism. The stereoisomer of dioctatin A that contains epimer at the 2-position has less aflatoxin production inhibitory activity.

<Other Step>

Examples of the other step include a step in which the dioctatin compound is mixed with pharmacologically acceptable known carrier, excipient, diluent, etc. to prepare the inhibitor with a desired form; and the like.

The aflatoxin production inhibitor of the present invention, produced by the method for producing an aflatoxin production inhibitor of the present invention, is suitably used for a method for controlling aflatoxin contamination, which will be described later.

(Method for Controlling Aflatoxin Contamination)

The method for controlling aflatoxin contamination of the present invention is a method that comprises using the aflatoxin production inhibitor of the present invention to thereby inhibit aflatoxin production by aflatoxin-producing microorganisms. The method for controlling aflatoxin contamination of the present invention is not particularly limited as long as it is a method that administers the aflatoxin production inhibitor to the object which the aflatoxin-producing microorganism has attached to or infected, and can be appropriately selected according to the purpose.

Examples of the object include plants, crops, and the like. Examples of the crop include grains such as maize, rice, buckwheat, and adlay; nuts such as peanut, pistachio nuts, and Brazil nut; spices such as nutmeg, pepper, and paprika; pulse such as coffee bean; and the like.

The method for administering the aflatoxin production inhibitor to the object which the aflatoxin-producing microorganism has attached to or infected is not particularly limited and can be appropriately selected according to the purpose. For example, the aflatoxin production inhibitor is prepared in the form of typical agricultural formulation and is applied or sprayed to the object which the aflatoxin-producing microorganism has attached to or infected.

The concentration of the dioctatin compound in the aflatoxin production inhibitor to be used in the method for controlling aflatoxin contamination is appropriately adjusted according to the type of or the degree of propagation of the aflatoxin-producing microorganism, and is, for example, preferably from 10 ppm to 50,000 ppm and more preferably from 100 ppm to 5,000 ppm.

EXAMPLES

Hereinafter, Examples of the present invention will be described, which however shall not be construed as limiting the present invention thereto.

Example 1

<Production (1) of Aflatoxin Production Inhibitor>

A liquid culture medium (pH 7.4) consisting of 2% glycerol and 1.5% Pharmamedia (manufactured by Trader's Oil Mill Co.) was dispensed in 100 mL portions in a Erlenmeyer flask equipped with waffle. A loop of actinomycete, *Streptomyces* sp. SA-2581, which was cultured on an agar slant medium, was inoculated into the Erlenmeyer flask and incubated with shaking at 27° C. for 3 days. 400 mL of the resultant as seed culture was inoculated into a jar fermentor, into which 12 L of sterile liquid culture medium was placed, and cultured for 9 days under the conditions of 27° C., aeration 12 L/minute, and agitation 200 revolution/minute. Pronal 502 (Shin-Etsu Chemical Co., Ltd.) was added as an antifoaming agent according to necessary. The culture broth obtained was centrifuged and separated into the culture filtrate and mycelium.

11 L of the culture filtrate obtained by centrifugation (containing $7.9 \times 10^5$ units of dipeptidyl peptidase II (DPPII) inhibitor) was applied to a column of Diaion HP-20 (500 mL, manufactured by Mitsubishi Chemical Corporation) and 2 L of water was passed through the column, followed by elution with 2.5 L of acetone solution that contains 50% by volume of 0.1 M hydrochloric acid.

To 2.4 L of eluate obtained, was added 6 M sodium hydroxide solution for neutralization, and then acetone and water were removed by vacuum concentration to obtain syrupy concentrate.

Active fraction of the syrupy concentrate derived from culture filtrate was separated by centrifugal liquid liquid partition chromatography (ascending method of chloroform:methanol:0.017 M aqueous ammonia=5:6:4 (by volume)). Specifically, a stationary phase (the lower layer from chloroform:methanol:0.017 M aqueous ammonia=5:6:4 (by volume)) was filled into a partition cell, the partition cell was rotated, and a mobile phase (the upper layer from chloroform:methanol:0.017 M aqueous ammonia=5:6:4 (by volume)) was introduced. After the mobile phase passed out of the exit of the partition cell and the internal pressure of the cell reached constant, a sample of the syrupy concentrate dissolved with the mobile phase was introduced. The mobile phase was kept running, and active fractions were collected. Of the two active fractions collected, the active fraction eluted later (dioctatin A) was collected, concentrated and dried under reduced pressure to obtain a primary purified product of dioctatin A.

The primary purified product of dioctatin A was dissolved in a solution of the upper layer from chloroform:methanol:water=5:6:4 (by volume). Then, to this solution was added 1M hydrochloric acid until pH 3 to prepare a sample containing the dioctatin A hydrochloride as the aflatoxin production inhibitor.

The solution containing the dioctatin A hydrochloride was separated by centrifugal liquid liquid partition chromatography (descending method of chloroform:methanol:water=5:6:4 (by volume)), and active fractions were collected. Specifically, a stationary phase (the upper layer from chloroform:methanol:water=5:6:4 (by volume)) was filled into a partition cell, the partition cell was rotated, and a mobile phase (the lower layer from chloroform:methanol:water=5:6:4 (by volume)) was introduced. After the mobile phase passed out of the exit of the partition cell and the internal pressure of the cell reached constant, a sample containing the dioctatin A hydrochloride was introduced. The mobile phase was kept running, and a secondary purified product was separated and collected.

The secondary purified product obtained was concentrated under reduced pressure, the precipitate obtained was filtered, washed with water, then further washed with acetone and dried to thereby obtain 22 mg of pure product of the dioctatin A hydrochloride as the aflatoxin production inhibitor.

The yield was determined from DPPII inhibitory activity, and the yield of dioctatin A was 14.5%.

Comparative Production Example 1

<Production of Aflatoxin Production Inhibitor>

In the preparation of aflatoxin production inhibitor in Example 1, the syrupy concentrate derived from culture filtrate was extracted with butanol, washed with water, then neutralized by the addition of 1 M aqueous ammonia, and concentrated under reduced pressure. The concentrate obtained was dissolved in acidic methanol that contains hydrochloric acid, and neutralized by the addition of 1M aqueous ammonia to produce a precipitate. The precipitate obtained was collected by filtration, washed with water, and dried under reduced pressure to obtain crude powder. To this was added methanol, dissolved by adding 20% hydrochloric acid dropwise, and then silica gel was added, concentrated and dried under reduced pressure. Next, this was applied to a column into which silica gel was filled and eluted with a mixture of (chloroform:methanol:acetic acid=100:30:1 (by volume)), and active fractions were collected. Of the two active fractions collected, the active fraction eluted later (dioctatin A) was collected, concentrated and dried under reduced pressure to obtain a primary purified product of dioctatin A. This was dissolved in acidic methanol that contains hydrochloric acid, and 1M aqueous ammonia was added dropwise to thereby precipitate an active fraction. This was collected by filtration and washed with water, followed by drying under reduced pressure to obtain a pure product of dioctatin A hydrochloride.

The yield of dioctatin A of Comparative Reference Example 1, obtained without use of centrifugal liquid liquid partition chromatography, was evaluated in the same way as in Example 1, and the yield thereof was 5.5%. This was as low as about ⅓ of that of the aflatoxin production inhibitor of the present invention in Example 1, which was obtained with use of centrifugal liquid liquid partition chromatography.

Example 2

<Evaluation (1) of Inhibition of Aflatoxin Production>
—Preparation of Spore Suspension of Aflatoxin-Producing Microorganism—

*Aspergillus parasiticus* NRRL2999, as an aflatoxin-producing microorganism, was incubated on a slant medium of potato dextrose agar medium (PDA medium, manufactured by Nissui Pharmaceutical Co., Ltd.) at 27° C. for 14 days. After the incubation, spores on a lawn were scrapped off with a platinum loop and suspended in an aqueous solution of a 0.01% Tween 80 (manufactured by Sigma-Aldrich Co.) to prepare a spore suspension.

The diluted spore suspension was spread onto a PDA medium and incubated for 2 days. The colony number appeared was determined as the spore number in suspension.
—Measurement of Activity of Aflatoxin Production Inhibitor—

10 mL of PD medium (Difco, available from Becton, Dickinson and Company) was placed in a 100 mL Erlenmeyer flask and autoclaved. Then, the aflatoxin production inhibitor (dioctatin A hydrochloride), prepared in Example 1, was aseptically added in an amount of from 0 µg/mL to 5 µg/mL (from 0 µM to 26 µM). The aflatoxin production inhibitor was added by dissolving in 20 µL of methanol-hydrochloric acid (100:0.009 by volume) solution.

10 µL ($1.9 \times 10^4$ CFU) of spore suspension of the aflatoxin-producing microorganism was inoculated into the Erlenmeyer flask and statically incubated at 27° C. for 5 days. Then, culture broth was filtered through a gauze, and mycelium and culture supernatant were each collected.

7 mL of culture supernatant containing aflatoxin was extracted with 7 mL of chloroform three times, and the chloroform layers obtained were combined and concentrated on an evaporator. The residue concentrated was dissolved in 1 mL of tetrahydrofuran-1 M acetic acid (20:80 by volume) solution and subjected to HPLC analysis to determine the amount of aflatoxin. The HPLC analysis was performed using HPLC column (COSMOSIL 5C18-MS-2, 4.6 mm in diameter, 150 mm in length, manufactured by Nacalai Tesque, Inc.) and tetrahydrofuran-water (20:80 by volume) as a mobile phase at a is flow rate of 1.0 ml/min, and the wavelength for detection was 365 nm. The amount of aflatoxin was determined by calculating each peak area of aflatoxins $B_1$ and $B_2$ and adding these values. The results are shown in Table 5.

—Evaluation of Growth of Aflatoxin-Producing Microorganism—

In the measurement of aflatoxin production inhibitory activity, the mycelium after filtration, together with the gauze used in the filtration, was placed in a centrifuge tube (50 mL) at the bottom of which 4 g of dry cotton was placed, and centrifuged at 800 g for 5 minutes. Then, the total weight of mycelium and the gauze, and the weight of the gauze alone were measured. Mycelial weight was determined by subtracting the weight of the gauze alone from the total weight of mycelium and the gauze measured. The growth of the aflatoxin-producing microorganism was evaluated from the mycelial weight. The results are shown in Table 5.

TABLE 5

| Concentration of dioctatin A (μg/mL) | Amount of aflatoxin produced*[1] (m ± S.D., μg/mL) n = 4 | Mycelial weight*[2] (m ± S.D., g) n = 4 |
|---|---|---|
| 0 | 3.8 ± 1.5 | 0.27 ± 0.037 |
| 0.075 | 3.0 ± 1.4 | 0.28 ± 0.008 |
| 0.31 | 1.1 ± 0.08 | 0.25 ± 0.005 |
| 1.3 | 0.6 ± 0.2 | 0.28 ± 0.016 |
| 5.0 | 0.1 ± 0.01 | 0.27 ± 0.028 |

*[1]Total amount of aflatoxins $B_1$ and $B_2$
*[2]Values in terms of the weight per 10 mL of culture broth Table 5 indicates that the dioctatin compound, an aflatoxin production inhibitor of the present invention, inhibits aflatoxin production by aflatoxin-producing microorganism depending on the concentration and that the inhibitory activity is strong such that $IC_{50}$ is 0.17 μg/mL (0.43 μM). For the mycelial weight of aflatoxin-producing microorganism, even when 5 μg/mL (13 μM) of the aflatoxin production inhibitor, the concentration at which aflatoxin production is almost completely suppressed, was added, there was no difference compared to the case without addition, revealing that the growth is not suppressed. These results indicate that the aflatoxin production inhibitor specifically inhibits aflatoxin production by aflatoxin-producing microorganism.

Comparative Example 1

The dioctatin compound is known as a DPPII inhibitor. Thus, for both of Orn-Pip (Comparative Example 1) and Dab-Pip (Comparative Example 2) which are also known as a strong inhibitor of DPPII, the aflatoxin production inhibitory activity and the growth of aflatoxin-producing microorganism were evaluated in the same way as in Example 1.

As a result, neither Orn-Pip nor Dab-Pip inhibited aflatoxin production by the aflatoxin-producing microorganism at all even when added at concentrations as high as 20 μg/mL (50 μM). At the same concentrations, inhibition of growth of aflatoxin-producing microorganism was not observed.

Example 3

A kernel of raw peanut (about 0.6 g) was placed in a vial (16.5 mm in diameter×40 mm in height) and 0.5 mL of distilled water was added, to which was added dioctatin A prepared in Example 1. The dioctatin A was added as a methanol-hydrochloric acid (100:0.9) solution of the dioctatin A, the concentration of which was adjusted so as to be 10 μg/g or 30 μg/g relative to the total weight of the raw peanut and distilled water (about 1.1 g). As a control without the addition of the dioctatin A, 9 μl of methanol-hydrochloric acid (100:0.9) solution was added.

The opening of each vial was covered with aluminum foil and autoclaved at 120° C. for 15 minutes. Then, 10 μL (1.9× $10^4$ CFU) of spore suspension of *Aspergillus parasiticus* NRRL2999, prepared in the same way as in Example 1, was inoculated into each of the vials. These were statically incubated at 27° C. for 4 days, and after 4 days, the surface of the peanut in each vial was completely covered with fungus hyphae. Fungus grew satisfactorily whether the dioctatin A was added or not.

Each peanut, on the surface of which fungus had grown, was crushed well with a spatula after the addition of 5 mL of chloroform. The crushed peanuts were removed by filtration, and the chloroform solution obtained was concentrated. Then, 5 mL of tetrahydrofuran-1 M acetic acid (20:80) solution was added to the residue, and analyzed by HPLC (column: COSMOSIL 5C18-MS-2, 4.6 mm in diameter, 150 mm (manufactured by Nacalai Tesque, Inc.), mobile phase: tetrahydrofuran-water (20:80), flow rate: 1.0 mL/minute, detection: UV 365 nm). The amount of aflatoxin was determined by calculating each peak area of aflatoxins $B_1$ and $B_2$ and adding these values.

From the amount of the dioctatin A added and the amount of aflatoxin, the inhibitory activity of the dioctatin A on aflatoxin8 production was determined. The results are shown in Table 6.

TABLE 6

| Concentration of dioctatin A (μg/peanut kernel*[1]) | Amount of aflatoxin produced*[2] (μg/peanut kernel*[1]) |
|---|---|
| 0 | 67.2*[3] |
| 10 | 5.2*[3] |
| 30 | 0.7*[4] |

*[1]about 1.1 g
*[2]Total amount of aflatoxins $B_1$ and $B_2$ produced
*[3]Average value (n = 3)
*[4]Average value (n = 2)

The results of Table 6 indicate that when 10 μg/g of dioctatin A was added, the amount of aflatoxin produced was reduced to 1/10 or less compared to the case where dioctatin A was not added, and that when 30 μg/g of dioctatin A was added, the amount of aflatoxin produced was reduced to as low as 1/100. This reveals that dioctatin A does not affect the growth of aflatoxin-producing microorganism and inhibits aflatoxin production specifically and effectively.

Example 4

<Production (2) of Aflatoxin Production Inhibitor>

Dioctatin B that has a naturally occurring configuration was synthesized according to the following manner.

[1] Synthesis of (S)-3-aminooctanoic acid 10 mL of (S)—N-benzyl-1-phenylethylamine was dissolved in 150 mL of dehydrated tetrahydrofuran and cooled with dry ice-acetone, and 28 mL of butyllithium (1.6 M hexane solution) was added dropwise under nitrogen stream. After stirring for 30 minutes under cooling with dry ice-acetone, a solution in which 5.2 mL of 2-octenoic acid ethyl ester was dissolved in 20 mL of tetrahydrofuran was added dropwise and stirred further for 2 hours under cooling with dry ice-acetone.

Next, 40 mL of saturated ammonium chloride solution was added and stirred, the reaction solution obtained was concentrated on a rotary evaporator to remove most of the tetrahydrofuran, and then extracted with chloroform twice. Drying chloroform solution over anhydrous sodium sulfate followed by concentration gave a mixture of adduct and S—N-benzyl-1-phenylethylamine which was present excessively. This mixture was dissolved in hexane, injected into 200 mL silica gel column filled with hexane and developed with hexane and then with hexane-ether 50:3. UV absorbance was monitored and the first fraction that shows UV absorbance was collected and concentrated to obtain 6.2 g of adduct.

The adduct obtained was dissolved in a mixture of 16 mL of water, 4 mL of acetic acid, and 80 mL of methanol, to which 880 mg of 10% palladium hydroxide on carbon was added. Reduction at a hydrogen pressure of 40 psi for 16 hours gave 3-aminooctanoic acid ethyl ester. Catalyst was removed by filtration and the residue was concentrated, followed by addition of 60 mL of 4N hydrochloric acid and hydrolysis at 80° C. for 16 hours.

The reaction solution was concentrated to remove most of hydrochloric acid, then dissolved in water, adsorbed to a 100 mL column of ion exchange resin Dowex 50 (H form), washed with water, and then eluted with 2 N aqueous ammonia.

The eluate obtained was fractionated and fractions that gave positive ninhydrin reaction were collected, concentrated and evaporated to dryness. As a result, 1.9 g of (S)-3-aminooctanoic acid was obtained as a colorless solid. Analytical values are shown below.

$[\alpha]_D^{21}$ +29.1 (c=1, $H_2O$)
Literature value: $[\alpha]_D^{21}$ +31.1 (c=1.11, $H_2O$) Angew. Chem. Int. Ed. Volume 34, Pages 455-456 (1995)
NMR (D2O) 400 MHz 0.7 (3H, t) 1.1 to 1.3 (6H, m) 1.5 (2H, q) 2.25 (1H, q) 2.4 (1H, q) 3.3 (1H, m)

[2] Synthesis of (S)—N-Boc-3-aminooctanoic acid 930 mg of (S)-3-aminooctanoic acid prepared in the [1] was dissolved in 5.84 mL of water and 5.84 mL of dioxane, and 5.84 mL of 1 M NaOH and 5.84 mL of dioxane solution containing 1407 mg of Boc2O were alternately added with stirring under cooling with ice. After stirring for 1 hour at room temperature, the solution was concentrated under reduced pressure, and pH was adjusted to 3 with a 5% aqueous solution of KHSO4 and extracted with ethyl acetate three times. The ethyl acetate extract was washed with water, then dried over anhydrous sodium sulfate and concentrated under reduced pressure. The residue was allowed to cool overnight and to solidify to obtain (S)—N-Boc-3-aminooctanoic acid. The yield was 1472 mg. Analytical values are shown below.

$^1$H NMR (CDCl$_3$, 600 MHz) δ 0.87 (3H, t-like, J=6.9 Hz, H-8), 1.22 to 1.37 (6H, m), 1.43 (9H, Boc), 1.51 (2H, q, H-4), 2.55 (2H, m, H-2), 3.89 (1H, mH-3)

[3] Synthesis of (S)—N-Boc-3-aminooctanoyl-L-threonine methyl ester 580 mg of (S)—N-Boc-3-aminooctanoic acid prepared in the [2], 420 mg of L-threonine methyl ester hydrochloride, 1089 mg of Bop reagent, and 333 mg of HOBt were dissolved in 4.5 mL of dehydrated DMF, 0.97 mL of triethylamine was added with stirring under cooling with ice, stirred for 30 minutes under cooling with ice, and then stirred overnight at room temperature. 70 mL of ethyl acetate was added to the reaction solution obtained, washed with 10% aqueous solution of citric acid, 4% aqueous solution of sodium hydrogencarbonate, and saturated salt solution, dried over anhydrous sodium sulfate, followed by vacuum concentration. The residue was crystallized from ethyl acetate-hexane to obtain (S)—N-Boc-3-aminooctanoyl-L-threonine methyl ester. The yield was 544 mg. Analytical values are shown below.

$[\alpha]_D^{21}$=−14.8 (c=0.5, chloroform-methanol 1:1)
nmr CDCl$_3$ 400 MHz
0.9 (3H, t), 1.2 (threonine-Me, 3H, d) 1.25 to 1.6 (10H, m), 1.45 (Boc, 9H, s)

[4] Synthesis of (S)—N-Boc-3-aminooctanoyl-2-amino-2-butenic acid methyl ester 508 mg of (S)—N-Boc-3-aminooctanoyl-L-threonine methyl ester prepared in the [3] was dissolved in 14 mL of methylene chloride and 195 mg of methanesulfonyl chloride was added. Further, 0.99 mL of triethylamine was added dropwise under cooling with ice. The solution was stirred overnight at room temperature. Then, 70 mL of ethyl acetate was added, washed with 10% aqueous solution of citric acid, 4% aqueous solution of sodium hydrogencarbonate, and saturated salt solution, dried over anhydrous sodium sulfate, followed by vacuum concentration to obtain 468 mg of solid (S)—N-Boc-3-aminooctanoyl-2-amino-2-butenic acid methyl ester. Analytical values are shown below.

$^1$H NMR (CDCl$_3$, 600 MHz) δ 0.86 (3H, t-like, J=7.0 Hz, H-8), 1.42 (9H, s, Boc), 1.21 to 1.38 (6H, m, H-5, 6, 7), 1.55 (2H, m, H-4), 1.76 (3H d, J=7.3 Hz CH3-CH=), 2.48 to 2.61 (2H, mH-2), 3.75 (3H s COOCH3) 3.83 to 3.91 (1H, m, H-3), 7.1 (1H q, J=7.2 CH3-CH=)

[5] Synthesis of (S)—N-Boc-3-aminooctanoyl-(S)-3-aminooctanoyl-2-amino-2-butenic acid methyl ester 215.8 mg of (S)—N-Boc-3-aminooctanoyl-2-amino-2-butenic acid methyl ester, prepared in the [4], was dissolved in 4 mL of 4 M hydrochloric acid in dioxane, and allowed to react for 1 hour to remove the Boc group. The reaction solution was concentrated under reduced pressure and evaporated to dryness, to which 172.7 mg of (S)—N-Boc-3-aminooctanoic acid prepared in the [3], 297 mg of Bop reagent, and 82.8 mg of HOBt were added and dissolved in 2 mL of dehydrated DMF and 3 mL of methylene chloride. To the resulting solution, 0.28 mL of triethylamine was added with stirring under cooling with ice. After 30 minutes of stirring under cooling with ice, the solution was stirred at room temperature overnight. The reaction solution obtained became gelatinous, which was dissolved by the addition of 70 mL of chloroform, washed with 10% aqueous solution of citric acid, 4% aqueous solution of sodium hydrogencarbonate, and saturated salt solution, and dried over anhydrous sodium sulfate, followed by vacuum concentration to obtain 399 mg of crude product.

The crude product was dissolved in a small amount of chloroform, injected into 40 mL of silica gel column filled with chloroform and developed with chloroform and then with chloroform:methanol 40:1. UV absorbance was monitored and fractions that contain objective substance were collected and concentrated under reduced pressure to obtain 284 mg of (S)—N-Boc-3-aminooctanoyl-(S)-3-aminooctanoyl-2-amino-2-butenic acid methyl ester. Analytical values are shown below.

$^1$H NMR (CDCl$_3$, 600 MHz) δ 0.90 (6H, t-like, J=6.8 Hz, H-8), 1.43 (9H, s, Boc), 1.31 (12H, m, H-5, 6, 7), 1.55 (4H, m, H-4), 1.75 (3H d, J=7.4 Hz CH3-CH=), 2.31 (2H, m H-2), 3.75 (3H s COOCH3) 3.83 to 3.91 (2H, m, H-3), 6.76 (1H q, J=7.2 CH3-CH=)

[6] Synthesis of dioctatin B 178.3 mg of (S)—N-Boc-3-aminooctanoyl-(S)-3-aminooctanoyl-2-amino-2-butenic acid methyl ester prepared in the [5] was dissolved in 12 mL of methanol, and 1.433 mL of 1 M aqueous solution of lithium hydroxide was added and stirred overnight at room temperature. The solution was neutralized by the addition of 1.443 mL of 1 M hydrochloric acid, concentrated under reduced pressure and evaporated to dryness. To this, 5 mL of TFA was added, allowed to react for 1 hour at room temperature, and then concentrated under reduced pressure. The residue was dissolved in 9 mL of methanol, neutralized with 2 M aqueous ammonia, and left at rest overnight at room temperature, resulting in the precipitation of dioctatin B. This was filtered to obtain 54.6 mg of dioctatin B. Analytical values are shown below.

$[\alpha]_D^{25}$=+14.6 (c=1, AcOH)
Literature value: +15.0
nmr (to 3.4 mg was added two drops of 2 N hydrochloric acid, dissolved in methanol, then concentrated under reduced pressure and evaporated to dryness. The residue was dissolved in 6d-DMSO and measurement was performed.)

$^1$H NMR (DMSO, 400 MHz) δ 0.85 (3H t J=7.0), 0.87 (3H t J=7.0), 1.25 (16H, m), 1.49 (2H, m) 1.64 (3H d, J=7.0 CH3-CH=), 2.36 (2H, m) 2.41 (2H, m), 3.23 (1H, d like, J=3.3 Hz) 3.36 (1H m), 6.50 (1H, q J=7.0 Hz, CH3-CH=)

$^{13}$C NMR (D$_2$O, 400 MHz) δ 168.75, 168.40, 165.46, 131.41, 128.50, 48.12, 46.08, 40.50, 37.26, 33.47, 31.85, 31.00, 30.88, 24.92, 23.92, 21.91, 21.74, 13.80, 13.72, 13.42

Example 5

<Production of Aflatoxin Production Inhibitor (3)>
Dioctatin A that has a naturally occurring configuration was synthesized according to the following manner.

[1] Synthesis of (3S)-3-amino-2-methyloctanoic acid 10 mL of S—N-benzyl-1-phenylethylamine was dissolved in 150 mL of dehydrated tetrahydrofuran and cooled with dry ice-acetone, and 28 mL of butyllithium (1.6 M hexane solution) was added dropwise under nitrogen stream. The solution was stirred for 30 minutes under cooling with dry ice-acetone, and a solution, in which 5.2 mL of 2-octenoic acid ethyl ester was dissolved in 20 mL of tetrahydrofuran, was added dropwise and stirred further for 2 hours under cooling with dry ice-acetone.

Next, 16.75 g of methyl iodide was added dropwise and stirred in the dark for 1 hour under cooling, then dry ice-acetone bath was removed, and the solution was stirred overnight at room temperature.

The reaction solution obtained was concentrated on a rotary evaporator to remove most of the tetrahydrofuran and then extracted with chloroform twice. The chloroform solution was dried over anhydrous sodium sulfate and then concentrated to obtain a mixture of adduct and excessive S—N-benzyl-1-phenylethylamine. This mixture was dissolved in hexane, injected into 200 mL silica gel column filled with hexane and developed with hexane and then with hexane-ether 50:3. UV absorbance was monitored and the first fraction that shows UV absorbance was collected and concentrated to obtain 6.92 g of adduct.

The adduct obtained was dissolved in a mixture of 16 mL of water, 4 mL of acetic acid, and 80 mL of methanol, to which 988 mg of 10% palladium hydroxide on carbon was added. Reduction at a hydrogen pressure of 45 psi for 16 hours gave (S)-3-amino-2-methyloctanoic acid ethyl ester. Catalyst was removed by filtration and the residue was concentrated, followed by addition of 60 mL of 4N hydrochloric acid and hydrolysis at 80° C. for 16 hours.

The reaction solution obtained was concentrated to remove most of hydrochloric acid, then dissolved in water and adsorbed to a 100 mL column of ion exchange resin Dowex 50 (H form), washed with water, and then eluted with 2 N aqueous ammonia. The eluate was fractionated and fractions that gave positive ninhydrin reaction were collected, concentrated and evaporated to dryness to obtain 3.72 g of a stereoisomeric mixture of (3S)-3-amino-2-methyloctanoic acid as a pale yellow, viscous, oily substance.

[2] Separation of stereoisomeric mixture of (3S)-3-amino-2-methyloctanoic acid

The crude mixture of (3S)-3-amino-2-methyloctanoic acid of the [1] was dissolved in a mixture of 200 mL of water and 2 mL of acetic acid, injected into a column with 19 mm in diameter and 113 cm in height of Dowex 50 W×4 (200-400 mesh) equilibrated with pyridine-acetate buffer (32 mL of pyridine and 60 mL of acetic acid are adjusted to 1 L with water), developed with the same buffer solution and fractionated every 15 g. The eluate fractions were analyzed by the ninhydrin color reaction, positive fractions 59 to 68, 69 to 72, and 73 to 80, were each concentrated under reduced pressure and taken to dryness to obtain 347 mg, 123 mg, and 289 mg of colorless to pale yellow solids. Each solid was dissolved in deuterium oxide and nmr was measured. Fractions 59 to 68 and 73 to 80 are different to each other and fraction 69 to 72 is a mixture thereof.

Analytical values of the substance obtained from the fractions 59 to 68 (hereinafter, referred to as (3S)-3-amino-2-methyloctanoic acid type 1) are shown below.

nmr (D2O) δ 0.73 (3H, m), 1.1 (3H, d), 1.15-1.3 (6H, m) 1.51 (2H, m), 2.47 (2H, m), 3.2 (1H, q)

Analytical values of the substance obtained from the fractions 73 to 80 (hereinafter, referred to as (3S)-3-amino-2-methyloctanoic acid type 2) are shown below.

$[\alpha]^{25}_D$ +5.28 (c1.05, MeOH)
ESI MS m/z 174.15[M+H]$^+$
$^1$H NMR (D$_2$O, 600 MHz) δ 0.90 (3H, t-like, J=7.8 Hz, H-8), 1.19 (3H, d, J=7.6 Hz, H-9), 1.34 (4H, m, H-6, 7), 1.39 (1H, m, H-5a), 1.44 (1H, m, H-5b), 1.66 (2H, m, H-4), 2.60 (1H, dq, J=5.2, 7.6 Hz, H-2), 3.43 (1H, dt, J=7.4, 5.2 Hz, H-3)

$^{13}$C NMR (D$_2$O, 600 MHz) δ 14.7, 15.8, 21.0, 35.0, 45.6, 56.1, 185.1

[3] Synthesis of Boc-(3S)-3-amino-2-methyloctanoic Acid Type 2

420 mg of (3S)-3-amino-2-methyloctanoic acid type 2 prepared in the [2] was dissolved in 2.1 mL of water and 2.1 mL of dioxane, and 2.1 mL of 1 M NaOH and 2.1 mL of dioxane solution containing 504 mg of Boc$_2$O were alternately added with stirring under cooling with ice. After stirring for 1 hour at room temperature, the solution was concentrated under reduced pressure, and pH was adjusted to 3 with a 5% aqueous solution of KHSO4 and extracted with ethyl acetate three times. The ethyl acetate extract was washed with water, then dried over anhydrous sodium sulfate and concentrated under reduced pressure. The residue was allowed to cool overnight, resulting in solidification to obtain Boc-(3S)-3-amino-2-methyloctanoic acid type 2. The yield was 238 mg. Analytical values are shown below.

$[\alpha]_D^{25}$=−14.58 (c=1, EtOAc)
$^1$H NMR (CDCl$_3$, 600 MHz) δ 0.88 (3H, t, J=6.9), 1.17 (3H, d, J=7.2 Hz), 1.31 (6H, m), 1.44 (9H, s) Boc, 1.51 (2H, m) 4-CH2, 2.68 (1H, br s) 2-CH2, 3.80 (1H, br, s) 3-CH—NHBoc, 4.74 (1H, br, s) NH,

[4] Synthesis of Boc-(3S)-3S-3-amino-2-methyloctanoyl-(S)-3-aminooctanoyl-2-amino-2-butenic acid methyl ester The (S)—N— Boc-3-aminooctanoyl-2-amino-2-butenic acid methyl ester prepared in the [4] of Example 5 was dissolved in 6 mL of 4 M hydrochloric acid in dioxane and allowed to react for 1 hour at room temperature to remove the Boc group. The reaction solution was concentrated under reduced pressure and taken to dryness. To this, 314.7 mg, 264 mg of (3S)—N-Boc-3-amino-2-methyloctanoic acid type 2 prepared in the [3], 431 mg of Bop reagent, and 132.6 mg of HOBt were added and dissolved in 3 mL of dehydrated DMF and 4 mL of methylene chloride, and 0.408 mL of triethylamine was added with stirring under cooling with ice.

After 30 minutes of stirring under cooling with ice, the solution was stirred at room temperature overnight. The reaction solution obtained became gelatinous, which was dissolved by the addition of 100 mL of chloroform, washed with 10% aqueous solution of citric acid, 4% aqueous solution of sodium hydrogencarbonate, and saturated salt solution, and dried over anhydrous sodium sulfate, followed by vacuum concentration to obtain 956.4 mg of crude product. The crude product was dissolved in a small amount of chloroform, injected into 40 mL of silica gel column filled with chloroform and developed with chloroform and then with chloroform:methanol 30:1. UV absorbance was monitored and fractions that contain objective substance were collected and concentrated under reduced pressure to obtain 413.9 mg of Boc-(3S)-3S-3-amino-2-methyloctanoyl-(S)-3-aminooctanoyl-2-amino-2-butenic acid methyl ester. Analytical values are shown below.

$[\alpha]_D^{25}$=−0.9 (c=1, methanol)

$^1$H NMR (4d-MeOH, 400 MHz) δ 0.89 (3H, t-like, J=6.9 Hz), 0.90 (3H, t-like, J=6.5 Hz), 1.09 (3H, d, J=7.0 Hz, CH3-CH—CO, H-9), 1.31 (10H, m,), 1.75 (3H, d, CH3-CH=), 1.43 (9H, s, Boc), 2.26 (1H, m), 2.48 (2H, m), 3.63 (1H, m), 3.73 (3H, s, COOCH3), 4.21 (1H, m) 6.76 (1H, q, J=7.1CH3-CH=)

[5] Synthesis of dioctatin A 413.9 mg of Boc-(3S)-3-amino-2-methyloctanoyl-(S)-3-aminooctanoyl-2-amino-2-butenic acid methyl ester prepared in the [4] was dissolved in 40 mL of methanol, and 3.916 mL of 1 M aqueous solution of lithium hydroxide was added and stirred overnight at room temperature. The solution was neutralized by the addition of 3.916 mL of 1M hydrochloric acid, concentrated under reduced pressure and evaporated to dryness. To this, 10 mL of TFA was added, allowed to react for 1 hour at room temperature, and again concentrated under reduced pressure. The residue was dissolved in 20 mL of methanol, neutralized with 2 M aqueous ammonia, and left at rest overnight at room temperature, resulting in the precipitation of dioctatin A. This was filtered to obtain 101.9 mg of dioctatin A. Analytical values are shown below.

$[\alpha]_D^{25}$=−2.2 (c=1, AcOH)

nmr (5.5 mg was dissolved in 1 mL of methanol containing 20 μL of 1 M hydrochloric acid, and then evaporated to dryness. The residue was dissolved in 6d-DMSO and measurement was performed.)

$^1$H NMR (DMSO, 400 MHz) δ 0.84 (3H, t-like, J=6.7 Hz), 0.87 (3H, t-like, J=6.8 Hz), 1.06 (3H, m, CH3-CH—CO), 1.24 (10H, m,), 1.63 (3H, d, J=7.1 Hz, CH3-CH=), 2.35 (2H, m), 2.54 (1H, m), 3.16 (1H, m), 3.41 (2H, m) 4.06 (1H, br s.), 6.49 (1H, q, J=7.1 CH3-CH=)

$^{13}$C NMR (DMSO, 400 MHz) δ 172.8, 168.7, 165.5, 131.3, 128.5, 52.4, 46.0, 40.7, 40.4, 33.5, 31.0, 31.0, 30.7, 24.9, 23.6, 21.9, 21.8, 13.8, 13.7, 13.7, 13.5

Example 6

<Evaluation (2) of Inhibition of Aflatoxin Production>

For the dioctatin B synthesized in Example 4 and the dioctatin A synthesized in Example 5, aflatoxin production inhibitory activity was evaluated.

The spore suspension of aflatoxin-producing microorganism was prepared in the same way as in Example 2.

—Measurement of Activity of Aflatoxin Production Inhibitor—

Each aflatoxin production inhibitor was aseptically added to 1 mL of autoclaved PD liquid medium (Difco, available from Becton, Dickinson and Company) in an amount of from 0 μg/mL to 20 μg/mL. 10 μL (1.9×10$^4$ CFU) of the spore suspension of the aflatoxin-producing microorganism was inoculated into the resulting liquid medium and statically incubated at 27° C. for 3 days. As a culture vessel, 24-well plate (Iwaki, available from AGC TECHNO GLASS Co., Ltd.) was used and each aflatoxin production inhibitor was added as 20 μL of methanol-hydrochloric acid (100:0.009 by volume) solution.

50 μL of each culture broth obtained was diluted 1,000 fold with distilled water, and the amount of aflatoxin (total amount of aflatoxins $B_1$, $B_2$, $G_1$, and $G_2$) contained in 50 μL of diluted solution was determined with a commercially available ELISA kit (RIDASCREEN FAST Aflatoxin, manufactured by R-Biopharm AG). The experiment was performed in triplicate. From the average amount of aflatoxin contained in 3 samples of culture broth obtained after the cultivation with the addition of inhibitor with each concentration (B), and the amount of aflatoxin without the addition of inhibitor (A), inhibition % [((A)−(B))/(A)×100] was calculated. The IC$_{50}$ values (concentration that inhibits the production by 50%) shown in Table were calculated based on the inhibition % at each concentration obtained. Results are shown in Table 7.

TABLE 7

| Compound | IC$_{50}$ (μg/mL) |
| --- | --- |
| Dioctatin A (Example 5) | 4.6 |
| Dioctatin B (Example 4) | 5.1 |

The results of Table 7 indicate that the aflatoxin production inhibitor, which comprises dioctatin with a naturally occurring configuration prepared by synthesis, exhibits excellent aflatoxin production inhibitory activity.

Industrial Applicability

The aflatoxin production inhibitor of the present invention inhibits aflatoxin production specifically and efficiently and is highly safe. Thus, by administering to a variety of objects which an aflatoxin-producing microorganism has attached to or infected, aflatoxin production can be inhibited easily, and the aflatoxin production inhibitor of the present invention is suitably used for the method for controlling aflatoxin contamination of the present invention and is suitable particularly for the method for controlling aflatoxin contamination toward plants and crops.

The invention claimed is:

1. A method for inhibiting aflatoxin production, comprising
   applying an aflatoxin production inhibitor comprising at least one compound selected from the group consisting of a dioctatin represented by the following formula (I) and a derivative thereof to an aflatoxin-producing microorganism, so that aflatoxin production of the aflatoxin-producing microorganism is inhibited:

formula (I)

wherein, in the formula (I), R is selected from either hydrogen or methyl, and wherein the derivative is selected from the group consisting of salts of the dioctatin with a pharmaceutically acceptable cation at a carboxyl group of the dioctatin and salts of the dioctatin with a pharmaceutically acceptable anion at an amino group of the dioctatin.

2. The method for inhibiting aflatoxin production according to claim 1, wherein R is methyl and the dioctatin has the formula 3. The method for inhibiting aflatoxin production according to claim 1, wherein R is hydrogen and the dioctatin has the formula 4. A method for controlling aflatoxin contamination, comprising
applying an aflatoxin production inhibitor comprising at least one compound selected from the group consisting of a dioctatin represented by the following formula (I) and a derivative thereof to an aflatoxin-producing microorganism, so that aflatoxin production of the aflatoxin-producing microorganism is inhibited:

formula (I)

wherein, in the formula (I), R is selected from either hydrogen or methyl, and wherein the derivative is selected from the group consisting of salts of the dioctatin with a pharmaceutically acceptable cation at a carboxyl group of the dioctatin and salts of the dictation with a pharmaceutically acceptable anion at an amino group of the dioctatin.

5. The method for controlling aflatoxin contamination according to claim 4, wherein the aflatoxin production inhibitor is administered to a crop to thereby inhibit aflatoxin production by the aflatoxin-producing microorganism which has infected the crop.

* * * * *